US012702489B2

(12) United States Patent
Carrat et al.

(10) Patent No.: US 12,702,489 B2
(45) Date of Patent: Aug. 11, 2026

(54) SYSTEM FOR PLANNING THE INTRODUCTION OF A NEEDLE IN A PATIENT'S BODY

(71) Applicant: IMACTIS, Saint-Martin-d'Heres (FR)

(72) Inventors: Lionel Carrat, Saint Martin d'Heres (FR); Stephane Lavallee, Martin d'Uriage (FR); Ivan Bricault, Grenoble (FR); Florence Billet, Grenoble (FR); Patrick-Denis Simonovici, Grenoble (FR); Agnes Labadie, Grenoble (FR)

(73) Assignee: Imactis, La Tronche (FR)

( * ) Notice: Subject to any disclaimer, the term of this patent is extended or adjusted under 35 U.S.C. 154(b) by 867 days.

(21) Appl. No.: 17/898,277

(22) Filed: Aug. 29, 2022

(65) Prior Publication Data

US 2022/0409295 A1 Dec. 29, 2022

Related U.S. Application Data

(63) Continuation-in-part of application No. 15/518,859, filed as application No. PCT/EP2015/074180 on Oct. 19, 2015, now abandoned.

(30) Foreign Application Priority Data

Oct. 17, 2014 (EP) .................................... 14306660

(51) Int. Cl.
*A61B 34/20* (2016.01)
*A61B 34/10* (2016.01)
(Continued)

(52) U.S. Cl.
CPC ............. *A61B 34/20* (2016.02); *A61B 34/10* (2016.02); *A61B 90/11* (2016.02); *A61B 90/37* (2016.02);
(Continued)

(58) Field of Classification Search
CPC ................................ A61B 34/20; A61B 34/10
See application file for complete search history.

(56) References Cited

U.S. PATENT DOCUMENTS 7,182,083 B2 2/2007 Yanof et al.
8,585,598 B2 * 11/2013 Razzaque ............. A61B 90/37 600/439
(Continued)

FOREIGN PATENT DOCUMENTS

EP 2777564 A1 9/2014
WO 2010/086374 A1 8/2010
WO 2013/055707 A1 4/2013

OTHER PUBLICATIONS

European Search Report and Search Opinion received for EP Patent Application No. 14306660.3, mailed on Apr. 17, 2015, 6 pages.
(Continued)

*Primary Examiner* — Angela M Hoffa

(57) ABSTRACT

A system for planning introduction of a needle in a patient's body, includes a needle guide configured to be coupled to a needle and a localization system configured for tracking the needle guide with respect to the patient's body. The system includes a processor configured for determining a virtual position and orientation of the needle with respect to the 3D image using localization data of the needle guide, thereby defining a virtual needle having the virtual position and orientation, detecting a part of the needle that has already been inserted into the patient's body as a trace in the 3D medical image, computing a distance between the virtual needle and the detected needle, and determining a representation of the computed distance that can be displayed.

15 Claims, 9 Drawing Sheets

(51) Int. Cl.
*A61B 90/00* (2016.01)
*A61B 90/11* (2016.01)

(52) U.S. Cl.
CPC . *A61B 2034/107* (2016.02); *A61B 2034/2051* (2016.02); *A61B 2034/2072* (2016.02); *A61B 2090/367* (2016.02)

(56) References Cited

U.S. PATENT DOCUMENTS 8,611,985 B2 * 12/2013 Lavallee ............ A61B 17/3478 382/128
8,670,816 B2 3/2014 Green et al.
8,690,776 B2 * 4/2014 Razzaque ............. A61B 34/20 600/407
8,774,901 B2 7/2014 Velusamy et al.
9,398,936 B2 * 7/2016 Razzaque ............. A61B 34/20
9,795,319 B2 * 10/2017 Lavallee ................ A61B 5/062
10,136,951 B2 * 11/2018 Razzaque ............. A61B 34/25
10,849,694 B2 * 12/2020 Lavallee ................ A61B 90/37
11,464,575 B2 * 10/2022 Heaney .................. A61B 90/37
11,464,578 B2 * 10/2022 State ..................... G06T 19/003
11,510,734 B2 * 11/2022 Lavallee ................ A61B 90/03
11,510,735 B2 * 11/2022 Lavallee ................ A61B 34/20
2003/0220557 A1 11/2003 Cleary et al.
2005/0267359 A1 12/2005 Hussaini et al.
2009/0118640 A1 5/2009 Miller et al.
2010/0268067 A1 * 10/2010 Razzaque ............ A61B 8/4245 600/424
2011/0082363 A1 4/2011 Xu et al.
2011/0295109 A1 * 12/2011 Lavallee .......... A61B 17/00234 600/424
2012/0089008 A1 4/2012 Strehl et al.
2012/0101370 A1 * 4/2012 Razzaque .......... A61B 18/1815 600/424
2013/0197357 A1 * 8/2013 Green .................. A61B 90/361 600/424
2013/0345718 A1 12/2013 Crawford et al.
2014/0073914 A1 * 3/2014 Lavallee ............ A61B 17/3478 600/424
2014/0142425 A1 * 5/2014 Razzaque .......... A61B 18/1815 600/424
2014/0180074 A1 * 6/2014 Green ...................... A61B 1/04 600/424
2017/0128139 A1 * 5/2017 Razzaque .......... A61B 18/1477
2017/0224419 A1 * 8/2017 Carrat ................ A61B 17/3403
2018/0221098 A1 8/2018 Forsyth et al.
2018/0289344 A1 * 10/2018 Green .................. A61B 90/361
2019/0167354 A1 * 6/2019 Heaney .................. A61B 34/20
2019/0247130 A1 * 8/2019 State ...................... A61B 34/20
2023/0233264 A1 * 7/2023 State ..................... G06T 19/003 600/424

OTHER PUBLICATIONS

International Preliminary Report on Patentability received for PCT Patent Application No. PCT/EP2015/074180, mailed on Apr. 27, 2017, 8 pages.
International Search Report and Written Opinion received for PCT Patent Application No. PCT/EP2015/074180, mailed on Jan. 27, 2016, 10 pages.

* cited by examiner

SYSTEM FOR PLANNING THE INTRODUCTION OF A NEEDLE IN A PATIENT'S BODY

CROSS REFERENCE TO RELATED APPLICATIONS

The present application is a continuation-in-part application of U.S. patent application Ser. No. 15/518,859, filed Apr. 13, 2017, which is a 35 U.S.C. 371 national stage application of PCT International Application No. PCT/EP2015/074180, filed Oct. 19, 2015, which claims the benefit of European Application No. 14306660.3, filed Oct. 17, 2014, the entire disclosure of which is incorporated by reference.

FIELD OF THE INVENTION

The invention relates to a system for planning the introduction of a needle in a patient's body.

BACKGROUND OF THE INVENTION

Surgical interventions performed in interventional radiology consist in introducing one or more surgical instruments, such as a needle or equivalent, in the body of the patient.

The interventional radiologist uses an imaging system, most likely a Computed Tomography Scan (CT-Scan) or a Cone Beam Computed Tomography (CBCT) or a Magnetic Resonance Imaging system (MRI) to see the organs of the patient and choose the target for the tips and the trajectories to be followed by the needles to reach this target.

In order to help the interventional radiologist to reach the target, a navigation system is necessary. Such systems use a localization system based on optical, electromagnetic, radiofrequency, inertial, ultrasound or mechanical technology.

The objective of the localization system is to give the spatial position and orientation in real time of one or more trackers.

Document WO 2010/086374 describes a method for navigating a surgical instrument such as a needle in a 3D medical image of a patient. To that end, the needle is slidingly arranged in a surgical guide to which a tracker is rigidly attached, and a reference marker is attached to the patient's body and localized by the localization system. Since the reference marker can be detected in the 3D medical image, it is possible to determine the position and orientation of the surgical guide with respect to the 3D medical image. The needle being a linear instrument, its axis is supposed to coincide with the axis of the guide. Hence, even if the needle is not itself tracked, the system allows determining the position and orientation of the needle axis in the 3D medical image.

A goal of interventional radiology is to hit a target that moves with the respiration of the patient. As shown in FIG. 1, the 3D medical image 1 used by the radiologist to plan the position and orientation of the needle to insert or to push deeper in the body of the patient corresponds to a given time of the respiratory cycle. Moreover, the 3D medical image 1 may contain some patient motion or registration errors. Thus, the virtual needle 2*v* may not match very well with the detected needle 2' in the 3D medical image and it can move according to the respiration of the patient, as illustrated by the double arrow. The time at which to push again the needle in the body of the patient in order to reach the target T is thus difficult to estimate.

Another goal of interventional radiology is to destroy unwanted cells such as tumours. In order to perform this destruction, more than one needle is sometimes required and these needles have to be placed such that the entire target tumour will be covered and then destroyed. However, as shown in FIG. 2, when there is already one or more needles 2*a'*, 2*b'*, 2*c'* inserted in the body of the patient with their tip in the target T, it is difficult to the radiologist to interpret what happens in three dimensions for all needles.

BRIEF DESCRIPTION OF THE INVENTION

A goal of the invention is to plan the introduction of a needle in a patient's body using one or more needles already partially or fully inserted in the patient body and detected in a 3D medical image.

According to a first aspect, a needle is already partially inserted in the body of the patient and the invention provides additional guidance to take into account the respiration of the patient to insert deeper the needle in the body of the patient.

The system for planning introduction of said needle in a patient's body comprises:

- a needle guide configured to be coupled to the needle;
- a localization system configured for tracking the needle guide with respect to the patient's body, the localization system being coupled to (i) a needle tracker attached to the needle guide and (ii) a reference marker adapted to be attached to the patient's body to determine a spatial position and orientation of the needle guide relative to the reference marker;
- a processor configured for
  - determining a virtual position and orientation of the needle with respect to the 3D image using localization data of the needle guide, thereby defining a virtual needle having said virtual position and orientation,
  - detecting a part of the needle that has already been inserted into the patient's body as a trace in the 3D medical image,
  - computing a distance between the virtual needle and the detected needle, and
- determining a representation of the computed distance;
- a display coupled to the processor for displaying a representation of the virtual needle and the representation of the computed distance between the virtual needle and the detected part of the needle.

According to a second aspect, one or more needles are already inserted in the patient body and the invention provides additional guidance to plan the insertion of a new needle in the body of the patient.

The system for planning introduction of said new needle in the patient's body comprises:

- a needle guide configured to be coupled to the needle;
- a localization system configured for tracking the needle guide with respect to the patient's body, the localization system being coupled to (i) a tracker attached to the needle guide and (ii) a reference marker adapted attached to the patient's body to determine a spatial position and orientation of the needle guide relative to the reference marker;
- a processor configured for
  - determining a virtual position and orientation of the needle with respect to the 3D image using localization data of the needle guide, thereby defining a virtual needle having said virtual position and orientation, detecting at least one inserted needle as a trace in the 3D medical image, and computing a distance between the virtual needle and the detected needle, wherein the trace detected in the 3D medical image is a trace of an additional needle distinct from the virtual needle and that has already been inserted into the patient's body; and a display coupled to the processor for displaying a representation of the virtual needle and a representation of the computed distance between the virtual needle and the at least one detected additional needle.

The needle guide may advantageously be selected from:

(i) a guide in which the needle is intended to be slidingly arranged, said guide comprising a tracker configured to be tracked by the localization system;

(ii) a guide intended to be rigidly attached to the needle, said guide comprising a tracker configured to be tracked by the localization system; and (iii) a tracker configured to be tracked by the localization system, said tracker being intended to be arranged inside the needle.

According to an embodiment, the processor is configured to implement an image processing algorithm to detect the at least one inserted needle.

The processor may further be configured to detect the at least one inserted needle by using the localization system for an initialization of the detected needle position and orientation.

According to the first aspect, the trace detected in the 3D medical image is a trace of a part of a needle that has already been inserted into the patient's body.

In such case, the processor may be configured for:

determining an instant of the respiratory cycle of the patient at which the virtual needle is closest to the detected needle; and registering the virtual position of the needle at said instant to the detected needle;

and the display may be configured for displaying again a representation of the distance between the virtual needle and the detected needle.

The processor may further be configured for determining an instant of the respiratory cycle of the patient at which the virtual needle is closest to the detected needle and providing an information to a user to push the needle into the patient's body at said instant.

According to an embodiment, the representation of the computed distance between the virtual needle and the detected needle comprises an indication of at least one 2D or 3D distance selected from:

(i) a 3D distance from a 3D point of the detected needle to a 3D point of the virtual needle;

(ii) a 3D distance between a line representing the detected needle to a line representing the virtual needle;

(iii) a 3D distance between either a 3D point of the detected needle and a line representing the virtual needle or a 3D point of the virtual needle and a line representing the detected needle;

(iv) 3D distances between either points of the detected needle and a plane containing the virtual needle or points of the virtual needle and a plane containing the detected needle;

(v) a 3D distance between either a line representing the detected needle and a plane containing the virtual needle or a line representing the virtual needle and a plane containing the detected needle; and (vi) a 2D distance between either the virtual needle and a projection of the detected needle in a plane containing the virtual needle or the detected needle and a projection of the virtual needle in a plane containing the detected needle.

The display and/or the processor may be configured for displaying said at least one 2D or 3D distance in at least one of the following formats:

a number corresponding to the numerical value of said distance;

a gauge with extremities corresponding to a function of the maximum and the minimum of these 3D distances along the respiratory cycle;

a curve showing the evolution of the distance with time;

a set of transparency levels of the detected needle in 3D or of a projection of the detected needle in the plane containing the virtual needle;

a set of thickness levels of the detected needle in 3D or of the projection of the detected needle in the plane containing the virtual needle;

a circle displayed on a plane containing the virtual needle, centered on the projection of the tip of the detected needles on the given plane and which radius is a function of said indicated 2D or 3D distance.

According to the second aspect, the trace detected in the 3D medical image is a trace of a needle distinct from the virtual needle and that has already been inserted into the patient's body.

In such case, the representation of the computed distance between the virtual needle and the at least one detected needle comprises an indication of at least a 2D or 3D distance selected from:

(i) a 3D distance from a 3D point of a detected needle to a respective 3D point of the virtual needle;

(ii) a 3D distance between the line corresponding to a detected needle to a line representing the virtual needle;

(iii) a 3D distance between either a 3D point of a detected needle and a line representing the virtual needle or a 3D point of the virtual needle and a line representing a detected needle;

(iv) 3D distances between either points of a detected needle and a plane containing the virtual needle or points of a virtual needle and a plane containing a detected needle;

(v) a 3D distance between either a line representing a detected needle and a plane containing the virtual needle or a line representing the virtual needle and a plane containing one detected needle;

(vi) a 2D distance between either the virtual needle and a projection of a detected needle in a plane containing the virtual needle or a detected needle and a projection of the virtual needle in a plane containing said detected needle; and (vii) a 3D distance between the tips of the detected needles.

The display and/or the processor may be further configured to display at least one 2D or 3D distance in at least one of the following formats:

a number corresponding to the numerical value of said distance;

a curve showing the evolution of the distance with time;

a set of transparency levels of the detected needles in 3D or of the projection of the detected needles in a plane containing the virtual needle;

a set of thickness levels of the detected needles in 3D or of the projection of the detected needles in a plane containing the virtual needle;

a sphere centered on the tip of the detected needles and whose radius is a function of said distance;

a circle displayed on a plane containing the virtual needle, centered on the projection of the tip of the detected needles on the given plane and which radius is a function of said distance.

The processor is advantageously further configured for determining an instant of the respiratory cycle of the patient where the virtual needle is at an optimal position relative to each detected needles and providing an information to a user to push the needle into the patient's body at said instant.

The system described above allows implementing a method for planning the introduction of a needle in a patient's body, wherein the needle is coupled to a needle guide tracked by a localization system with respect to a 3D medical image of the patient, comprising:

determining a virtual position and orientation of the needle with respect to the 3D image using localization data of the needle guide;

detecting at least one inserted needle as a trace in the 3D medical image;

displaying a representation of the virtual needle and a representation of a relative position of the virtual needle with respect to the at least one detected needle.

The needle guide is selected from:

(i) a guide in which the needle is slidingly arranged, said guide comprising a tracker configured to be tracked by the localization system;

(ii) a guide rigidly attached to the needle, said guide comprising a tracker configured to be tracked by the localization system; and (iii) a tracker configured to be tracked by the localization system, said tracker being arranged inside the needle.

According to an embodiment, the at least one inserted needle is detected with an image processing algorithm.

Alternatively, the at least one inserted needle is detected by using the localization system for an initialization of the detected needle position and orientation.

According to a first aspect, the trace detected in the 3D medical image is a trace of a part of the navigated needle that has already been inserted into the patient's body.

Advantageously, the method may comprise the following steps:

determining an instant of the respiratory cycle of the patient at which the virtual needle is closest to the detected needle;

registering the virtual position of the needle at said instant to the detected needle; displaying again a representation of the virtual needle with respect to the detected needle.

Advantageously, the method may comprise determining an instant of the respiratory cycle of the patient at which the virtual needle is closest to the detected needle and providing an information to a user to push the needle into the patient's body at said instant.

The representation of the relative position of the virtual needle with respect to the detected needle comprises an indication of at least one 2D or 3D distance selected from:

(i) a 3D distance from a 3D point of the detected needle to a 3D point of the virtual needle;

(ii) a 3D distance between a line representing the detected needle to a line representing the virtual needle;

(iii) a 3D distance between either a 3D point of the detected needle and a line representing the virtual needle or a 3D point of the virtual needle and a line representing the detected needle;

(iv) 3D distances between either points of the detected needle and a plane containing the virtual needle or points of the virtual needle and a plane containing the detected needle;

(v) a 3D distance between either a line representing the detected needle and a plane containing the virtual needle or a line representing the virtual needle and a plane containing the detected needle; and (vi) a 2D distance between either the virtual needle and a projection of the detected needle in a plane containing the virtual needle or the detected needle and a projection of the virtual needle in a plane containing the detected needle.

Said at least one 2D or 3D distance may be displayed in at least one of the following formats:

a number corresponding to the numerical value of said distance;

a gauge with extremities corresponding to a function of the maximum and the minimum of these 3D distances along the respiratory cycle;

a curve showing the evolution of the distance with time;

a set of transparency levels of the detected needle in 3D or of a projection of the detected needle in the plane containing the virtual needle;

a set of thickness levels of the detected needle in 3D or of the projection of the detected needle in the plane containing the virtual needle;

a circle displayed on a plane containing the virtual needle, centered on the projection of the tip of the detected needles on the given plane and which radius is a function of said indicated 2D or 3D distance.

According to a second aspect, the trace detected in the 3D medical image is a trace of a needle distinct from the virtual needle and that has already been inserted into the patient's body.

The representation of the relative position of the virtual needle with respect to the at least one detected needle comprises an indication of at least a 2D or 3D distance selected from:

(i) a 3D distance from a 3D point of a detected needle to a respective 3D point of the virtual needle;

(ii) a 3D distance between the line corresponding to a detected needle to a line representing the virtual needle;

(iii) a 3D distance between either a 3D point of a detected needle and a line representing the virtual needle or a 3D point of the virtual needle and a line representing a detected needle;

(iv) 3D distances between either points of a detected needle and a plane containing the virtual needle or points of a virtual needle and a plane containing a detected needle;

(v) a 3D distance between either a line representing a detected needle and a plane containing the virtual needle or a line representing the virtual needle and a plane containing one detected needle;

(vi) a 2D distance between either the virtual needle and a projection of a detected needle in a plane containing the virtual needle or a detected needle and a projection of the virtual needle in a plane containing said detected needle; and (vii) a 3D distance between the tips of the detected needles.

Said at least one 2D or 3D distance being displayed in at least one of the following formats:

a number corresponding to the numerical value of said distance;

a curve showing the evolution of the distance with time;

- a set of transparency levels of the detected needles in 3D or of the projection of the detected needles in a plane containing the virtual needle;
- a set of thickness levels of the detected needles in 3D or of the projection of the detected needles in a plane containing the virtual needle;
- a sphere centered on the tip of the detected needles and whose radius is a function of said distance;
- a circle displayed on a plane containing the virtual needle, centered on the projection of the tip of the detected needles on the given plane and which radius is a function of said distance.

The method may further comprise determining an instant of the respiratory cycle of the patient where the virtual needle is at an optimal position relative to each detected needle and providing an information to a user to push the needle into the patient's body at said instant.

Another object of the invention is a computer program product comprising computer-readable instructions which, when loaded and executed on the processor of a system as described above, perform the steps of:

- determining a virtual position and orientation of the needle with respect to the 3D image using localization data of the needle guide;
- detecting at least one inserted needle as a trace in the 3D medical image;
- computing a distance between the virtual needle and the detected needle.

BRIEF DESCRIPTION OF THE DRAWINGS

Other features and advantages of the invention will be apparent from the following description, in connection with the appended drawings wherein.

DETAILED DESCRIPTION OF EMBODIMENTS

The general context of the present disclosure is the planning of the introduction of a needle in a patient's body, the needle being coupled to a needle guide tracked by a navigation system with respect to a 3D medical image of the patient.

Thanks to the navigation system, a virtual needle can be computed, that has a virtual position and orientation with respect to the 3D image computed based on localization data (position and orientation) of the needle guide.

Besides, a portion of a needle (which can be the currently navigated needle or a previously inserted needle) that has been inserted into the patient's body can be detected as a trace in the 3D image.

A distance between the virtual needle and the detected needle (trace) can thus be computed and used to guide the insertion of the needle toward a target, possibly taking into account previously inserted needles, if any.

Figures 1, 2:
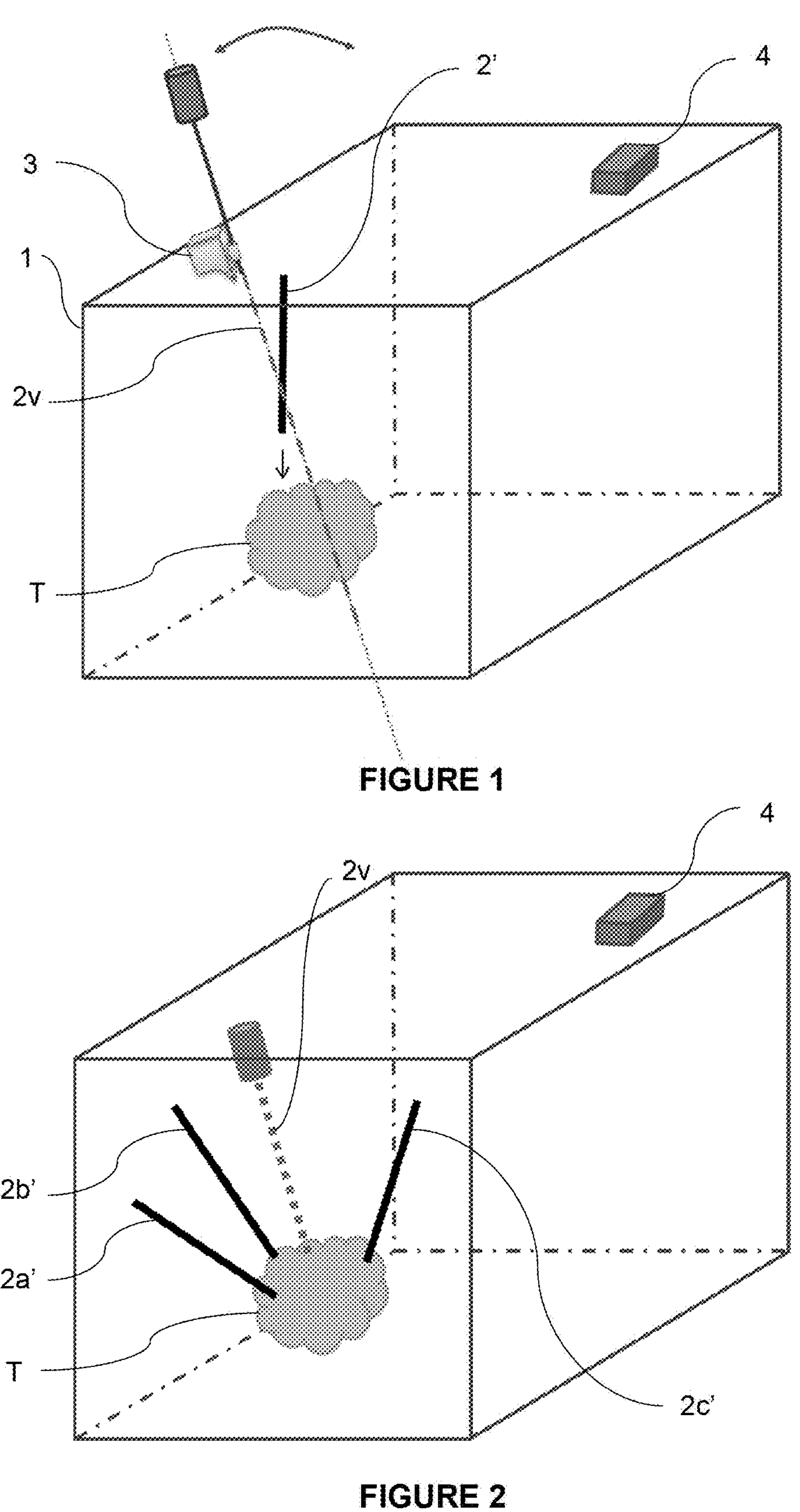
FIG. 1 illustrates a situation where a navigated needle has not been completely inserted into the patient's body and the virtual needle does not match with the detected needle part already inserted.
FIG. 2 illustrates a situation where a navigated needle has to be inserted into the patient's body wherein several needles have already been inserted in the target.
Figure 3:
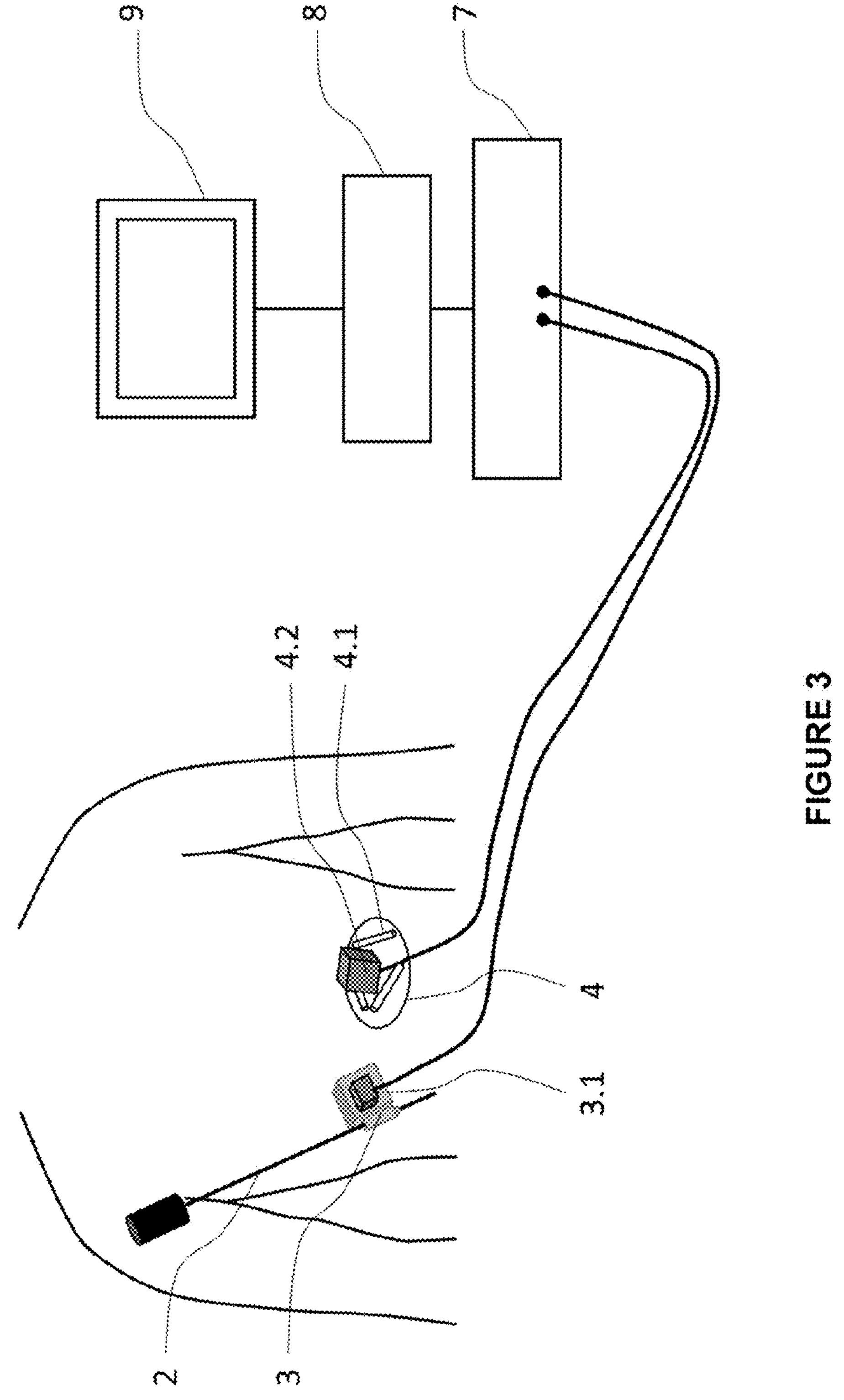
FIG. 3 schematically illustrates a navigation system according to the invention.

As shown in FIG. 3, the method is implemented by a navigation system comprising a processor 8 and a display 9 coupled to the processor 8 for displaying in particular information computed by the processor.

The processor is configured to receive a 3D image of the patient, with at least one needle or portion of needle already inserted into the patient's body.

The navigation system further comprises a localization system 7 coupled to the processor 8 to communicate localization data to the processor.

The localization system 7 is coupled to at least a needle tracker 3.1 attached to the needle guide 3 and a reference marker 4 attached to the patient's body.

Preferably, the localization system is based on electromagnetic technology, in particular in view of minimizing the size of the tracker attached to the needle guide. However, other technologies could be used, such as optical, radiofrequency, inertial, ultrasound or mechanical technology.

The reference marker 4 comprises an electromagnetic field generator 4.2 and a geometrical fiducials assembly 4.1 used for registration between patient and images, as will be described below.

The reference marker is preferably non-invasively attached to the patient; for example, the reference marker may be removably fixed to the patient's skin by an adhesive.

The tracker 3.1 attached to the needle guide is an electromagnetic sensor. For example, said sensor may be embedded in the needle guide.

The localization system comprises at least one electric current generator adapted to feed the electromagnetic field generator with electric current so that the electromagnetic field generator 4.2 emits an electromagnetic field that establishes a measurement volume. When an electromagnetic sensor, such as the tracker 3.1, enters said electromagnetic field, small electrical currents are generated in the sensor. Said currents are transmitted to the localization system 7 and received on an electronic card coupled to a processor of the localization system. The electronic card transforms said electric currents into signals that are sent to the processor of the localization system. Based on signals, the processor of the localization system 7 computes localization data that are the position and the orientation of the tracker 3.1 attached to the needle guide 3 relative to the magnetic field generator 4.2. In this way, the position and orientation of the needle guide 3 relative to the patient can be determined.

Said localization data is transmitted by the localization system 7 to the processor 8.

Since the needle 2 is either attached to the needle guide 3 or slidingly arranged within the needle guide 3 (i.e, the needle has an at least partially known position and/or orientation relative to the needle guide), the position and orientation of the needle relative to the patient can be indirectly known.

The geometric fiducials assembly 4.1 of the reference marker 4 is used for registration between the patient and the 3D medical image. The geometric fiducials are indeed designed to be visible in said image by being made of suitable materials and present a known geometry. For example, if the 3D image is acquired by an X-ray imaging system, the geometric fiducials are made in a radiopaque material. The geometric fiducials may be spherical, cylindrical (either solid or hollow), or have any recognizable shape. In addition, the spatial relationship between the geometric fiducials is also known. Embodiments of geometric fiducials are described in document WO 2010/086374, which is herein incorporated by reference.

During acquisition of the 3D medical image, the reference marker is attached to the patient's body so that the acquired image not only includes the patient's anatomy but also the geometric fiducials of the reference marker.

In this way, the position and orientation of the 3D image relative to the patient can be determined.

FIGS. 4A to 4E illustrate how registration between localization data and the 3D image can be achieved by the processor 8.

Figure 4A:
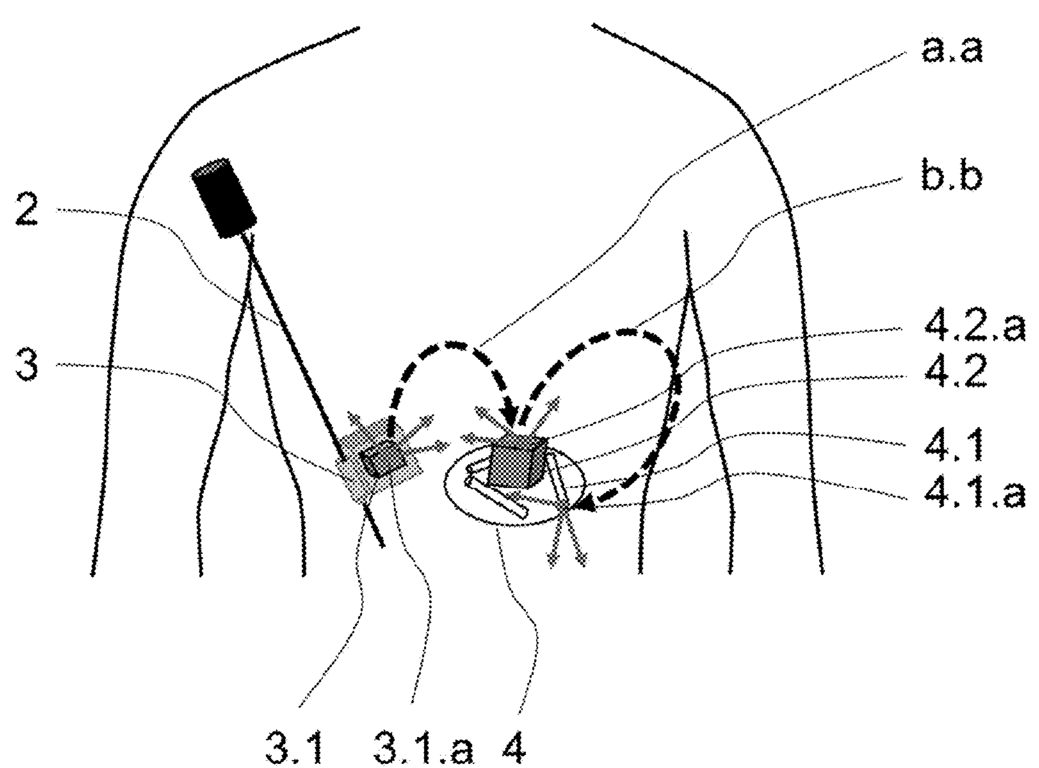
FIGS. 4A to 4E schematically illustrate how registration between the localization data and the 3D image of the patient can be done.

As shown in FIG. 4A, a 3D coordinate system 3.1.*a* is attached to the needle guide tracker 3.1, a 3D coordinate system 4.1.*a* is attached to the geometrical fiducials assembly 4.1 of the reference marker 4, and a 3D coordinate system 4.2.*a* is attached to the magnetic field generator 4.2 of the reference marker 4.

Figure 4B:
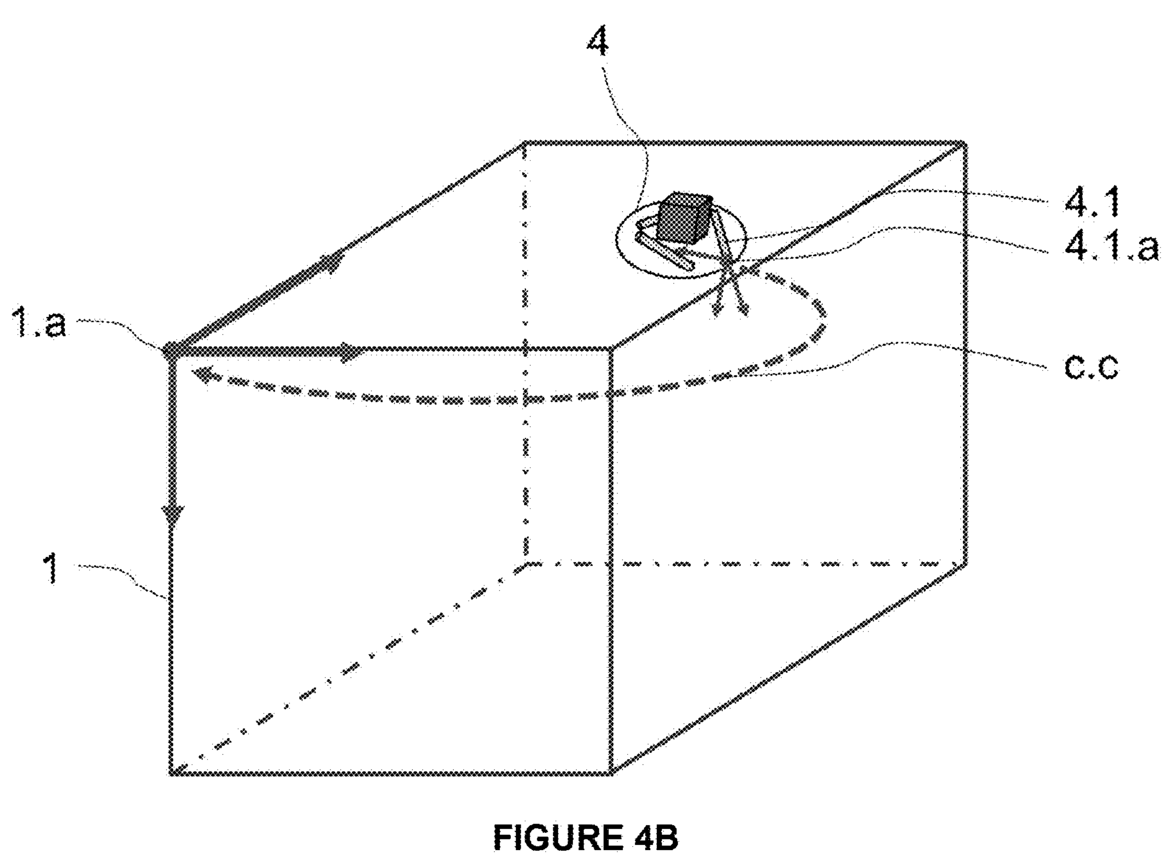
Figure 4C:
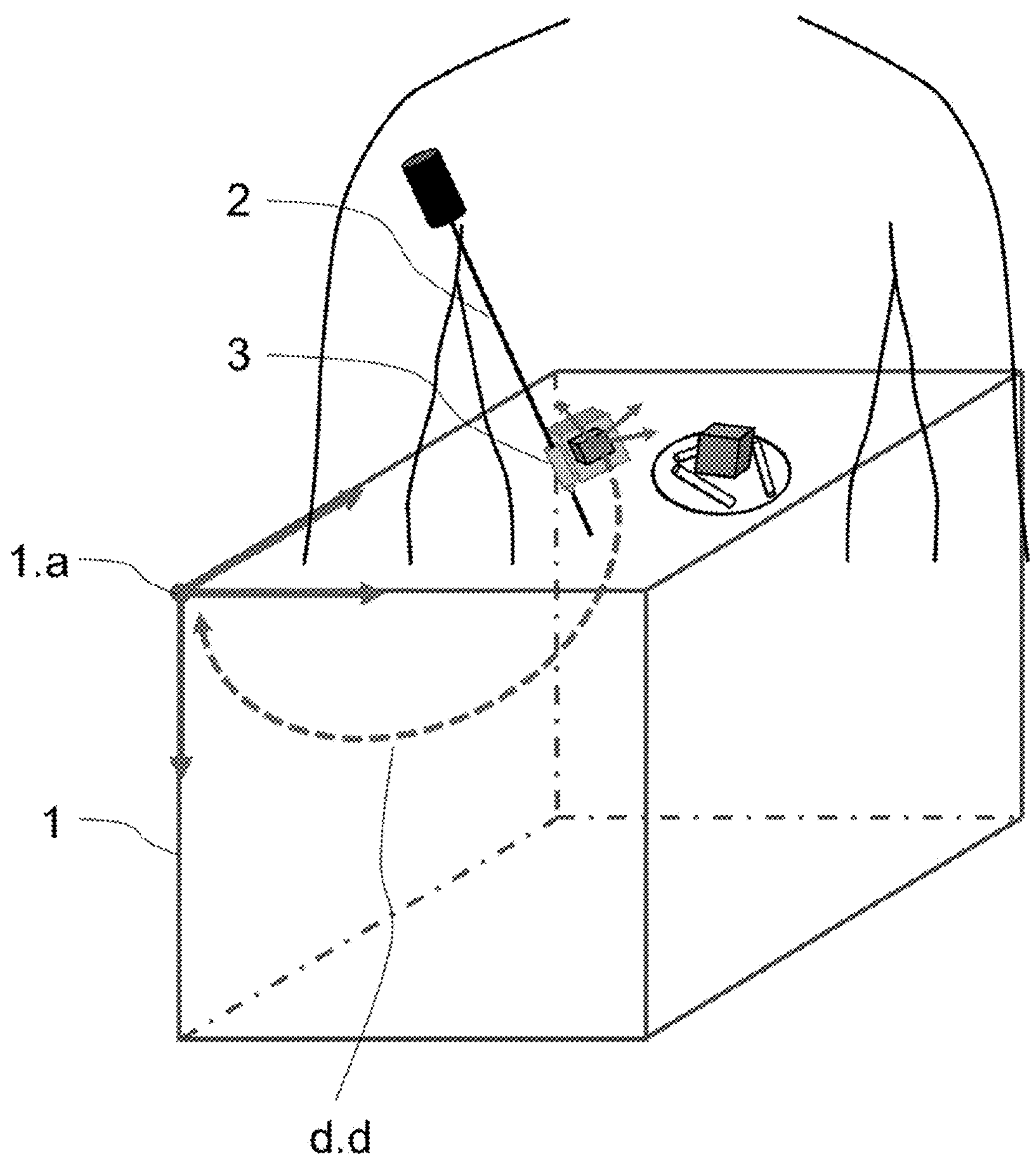
Figure 4D:
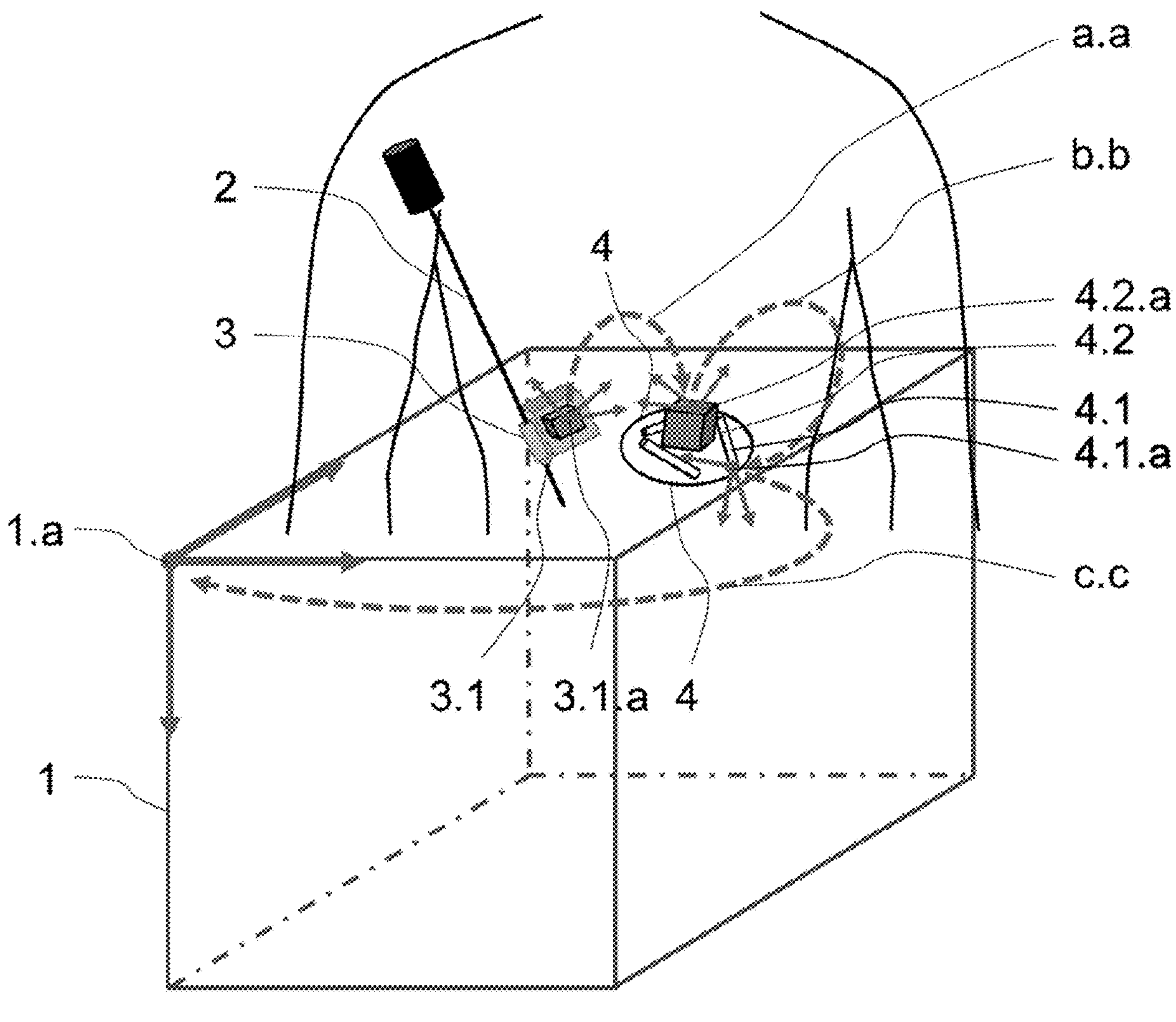
Figure 4E:
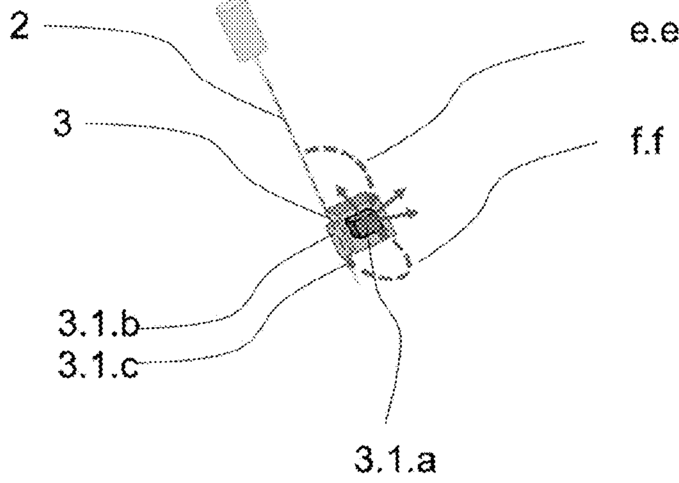

As shown in FIG. 4E, the needle guide 3 comprises a tip 3.1.*c* and an axis 3.1.*b* that coincides with the axis of the longitudinal axis of the linear instrument. The tip 3.1.*c* is located on the axis 3.1.*b*. The position and orientation of the needle guide tip 3.1.*c* and of the needle guide axis 3.1.*b* are known by manufacturing, using respectively matrices f.f and e.e, in the 3D coordinate system 3.1.*a* attached to the needle guide tracker 3.1.

Based on data provided by the localization system, the position and orientation of the needle guide tracker 3.1 are known in the coordinate system 4.2.*a* of the magnetic field generator 4.2, using matrix a.a.

The matrix b.b, which determines the position and orientation of the magnetic field generator 4.2 in the coordinate system 4.1.*a* of the geometric fiducials assembly 4.1, is known by manufacturing.

As a consequence, by combining matrices a.a and b.b, the needle guide tip and axis are known in the coordinate system 4.1.*a* of the geometrical fiducials assembly 4.1.

As the reference marker 4 is fixed on the patient during the image acquisition, geometrical fiducials are included in the patient image. By image processing, the geometrical fiducials can be detected in the image and as a consequence the matrix c.c between the coordinate system 4.1.*a* of the geometrical fiducials assembly 4.1 and the coordinate system 1.*a* of the 3D image 1 is known (see FIG. 4B).

By combining matrix a.a, matrix b.b and matrix c.c, it is possible to compute matrix d.d, which allows knowing the needle guide tip and axis in the coordinate system 1.*a* of the image 1 (see FIGS. 4C and 4D, FIG. 4D being a combination of FIGS. 4A-4C).

From the needle guide tip and axis, 2D images can be extracted from the 3D volume of patient image 1 and displayed on the screen 9.

Detecting a needle in a 3D image can be achieved using known image processing algorithms that detect line segments as a set of linearly arranged high brightness voxels in a volume of voxels.

Advantageously, the needle guide can be placed on an inserted needle to facilitate its detection. Then, the trace of the needle is detected by using the position of the needle guide in the 3D image given by the localization system for initializing the search of the detection algorithm. It makes the global process reliable and additionally enables, in case more than one needle are inserted in the patient, to determine which needle among several needles has to be detected and registered.

According to a first embodiment, the detected needle is the needle that is being navigated and introduced into the patient's body toward a target to be treated by the needle. At this stage, only a part of said needle has been introduced and the needle tip has not reached the target yet. The goal of the user is to place the needle tip in the target.

According to a second embodiment, the detected needle (s) is(are) different from the needle that is introduced into the patient's body and that is tracked in real-time. This corresponds for example to the treatment of a tumor by a plurality of needles, the tips of said needles being intended to be distributed optimally over the tumor volume so as to treat the whole tumor. At this stage, one or more needles have already been placed with their tip in the target and the goal of the user is to place the needle tip in the target taking into account the already inserted needles.

In both cases, the invention proposes to determine a position and orientation of the virtual needle with respect to the 3D image using localization data of the needle guide; to detect the at least one inserted needle as a trace in the 3D medical image; and to display a representation of the virtual needle and a representation of a relative position of the virtual needle with respect to the at least one detected needle.

The representation of said relative position involves the computation of a 2D or 3D distance between the at least one detected needle and the virtual needle. Such a 2D or 3D distance can be:

(i) a 3D distance from a 3D point of the at least one detected needle to a 3D point of the virtual needle;
(ii) a 3D distance between the line corresponding to the at least one detected needle to a line representing the virtual needle;
(iii) a 3D distance between either a 3D point of the at least one detected needle and a line representing the virtual needle or a 3D point of the virtual needle and a line representing the at least one detected needle;
(iv) 3D distances between either points of the at least one detected needle and a plane containing the virtual needle or points of the virtual needle and a plane containing the detected needle;
(v) a 3D distance between either a line representing a detected needle and a plane containing the virtual needle or a line representing the virtual needle and a plane containing the at least one detected needle;
(vi) a 2D distance between either the virtual needle and a projection of the at least one detected needle in a plane containing the virtual needle or the at least one detected needle and a projection of the virtual needle in a plane containing the at least one detected needle; or
(vii) if several needles are detected, a 3D distance between the tips of the detected needles.

In these distances, the above-mentioned 3D point can advantageously be the center of the active part of the needle, if said needle is a radiofrequency or a cryogeny needle.

The inserted needle can be detected in the 3D medical image by an image processing algorithm.

Figure 5:
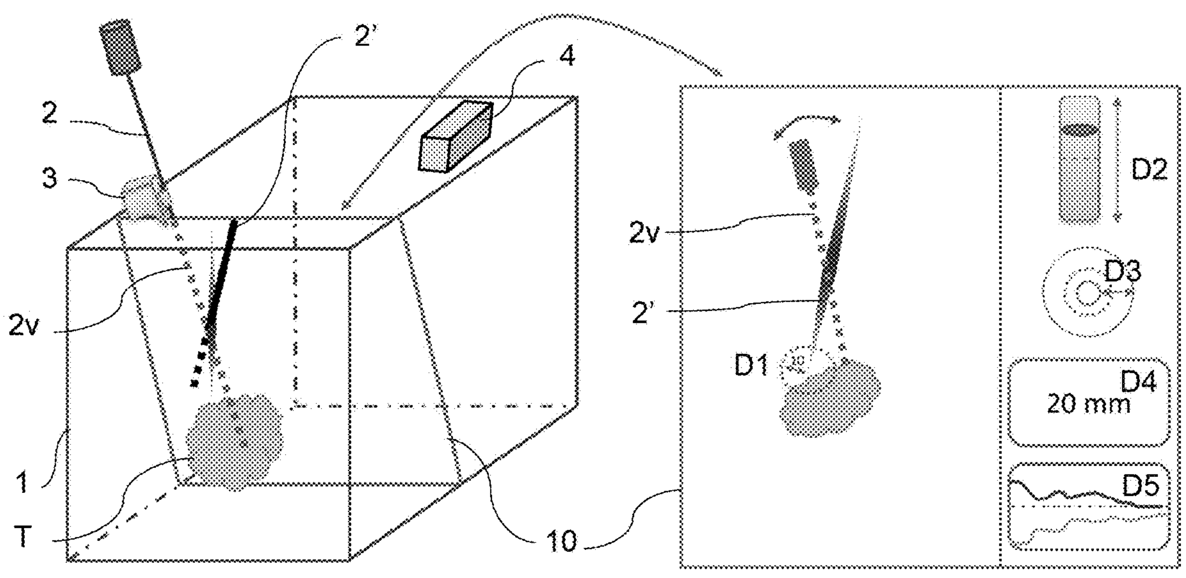
FIG. 5 illustrates an embodiment of a 2D display of a representation of the virtual needle with respect to the detected needle.
Figure 6:
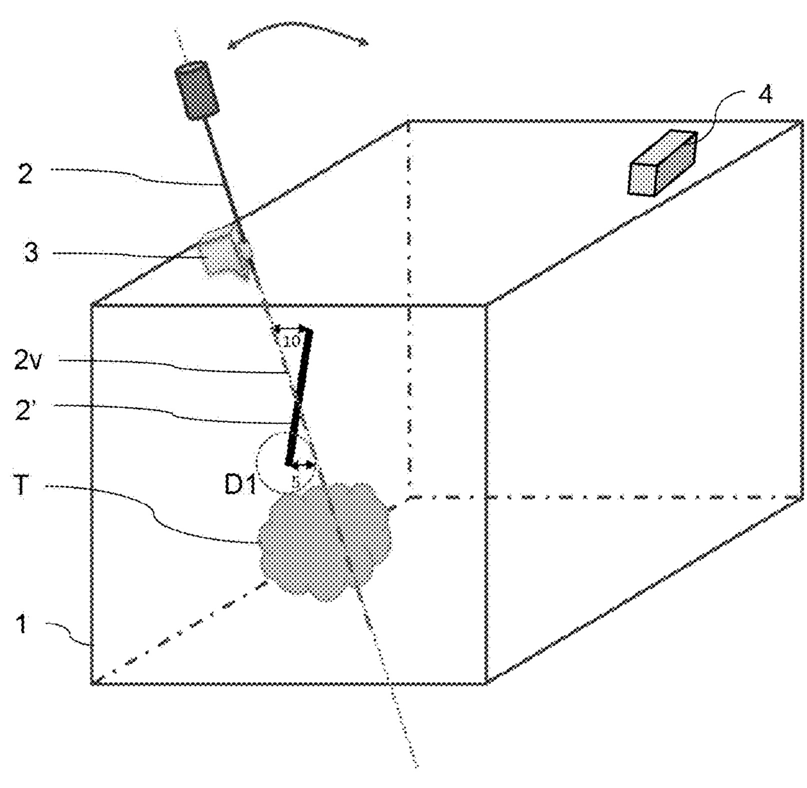
FIG. 6 illustrates an embodiment of a 3D display of a representation of the virtual needle with respect to the detected needle.
Figure 7:
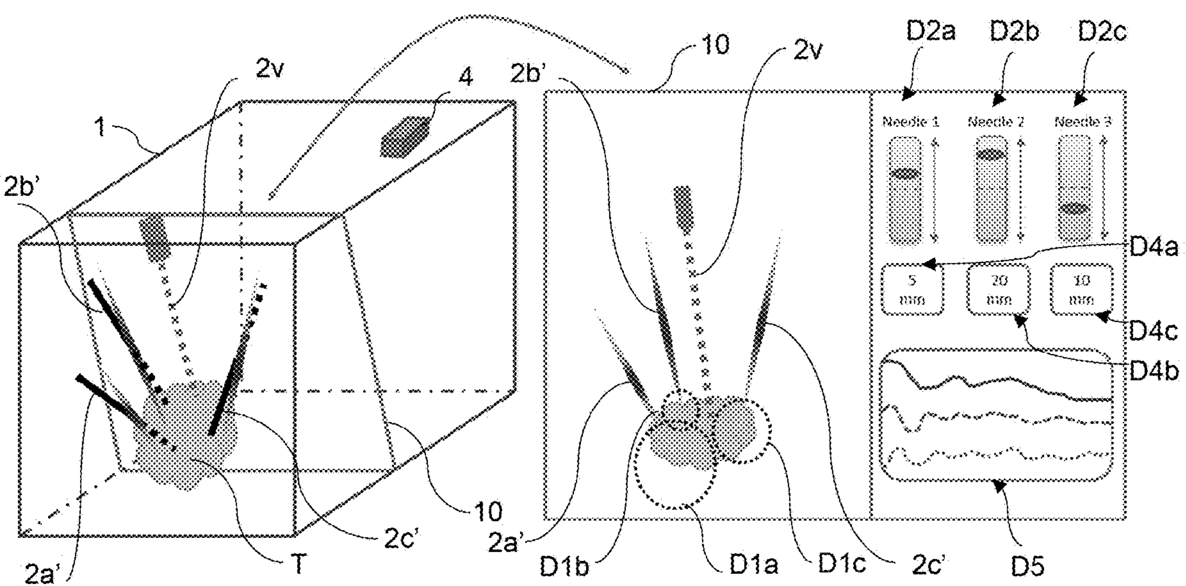
FIG. 7 illustrates an embodiment of a 2D display of a representation of the virtual needle with respect to a plurality of detected needles.
Figure 8:
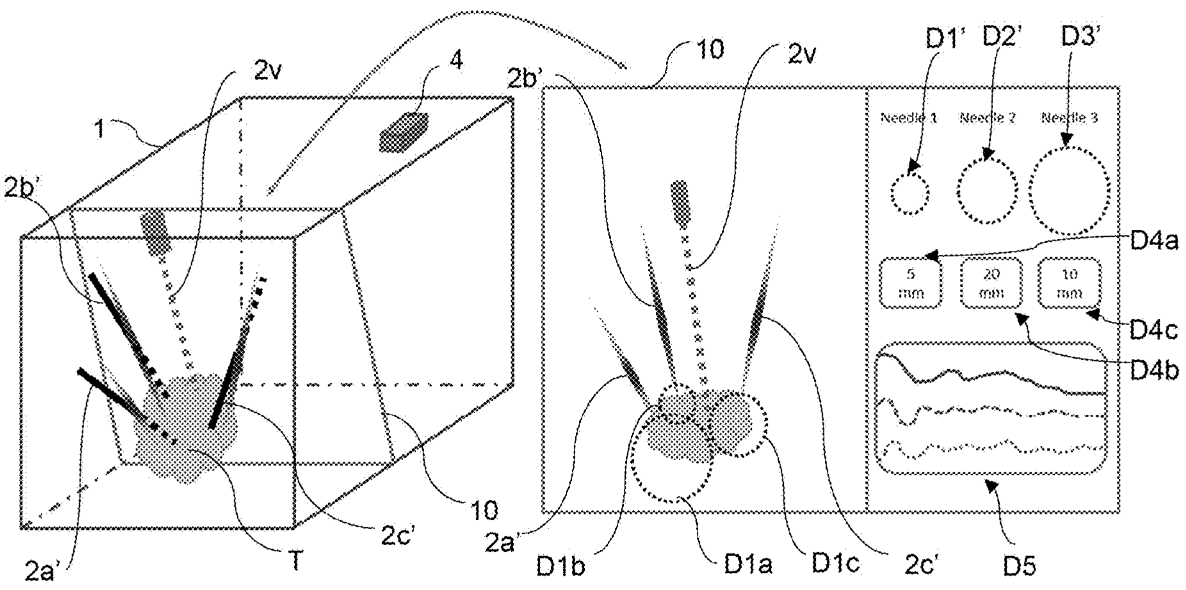
FIG. 8 illustrates an embodiment of a 2D display of a representation of the virtual needle with respect to a plurality of detected needles.
Figure 9:
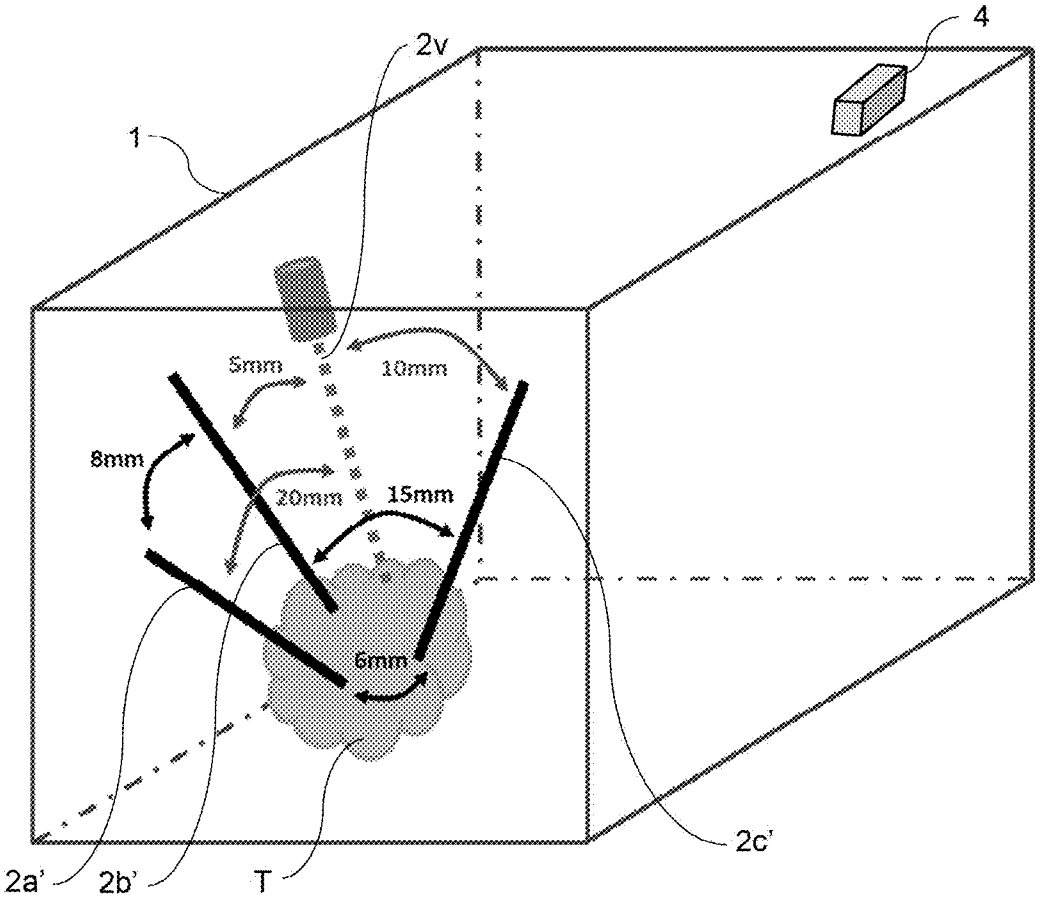
FIG. 9 illustrates an embodiment of a 3D display of a representation of the virtual needle with respect to a plurality of detected needles.

FIGS. 5 and 6 relate to the first embodiment; FIGS. 7 to 9 relate to the second embodiment.

Referring to FIG. 5 (left), the 3D image 1 contains a trace 2' of the already inserted needle.

This needle is coupled to a needle guide 3 which contains a tracker to be navigated with respect to the 3D image by the navigation system.

The reference 2*v* represents the virtual needle.

As shown in the right part of FIG. 5, a slice 10 according to a plane containing the axis of the virtual needle is displayed with the trace of the detected needle 2' projected in said plane and the target T.

On this slice 10 a circle D1 in dotted line is centered on the projection of the tip of the detected needle 2' in said slice. This circle has a radius which depends on the distance between said tip and the plane containing the axis of the virtual needle (this distance being calculated by the processor); the greater the distance, the larger the radius of this circle. The value of the radius of this circle (10 mm in the illustrated example) may also be displayed.

If the patient breathing generates motions of the partially inserted needle, this distance will vary along the respiratory cycle.

The distance may also be represented according to other formats.

For example, a gauge D2 whose upper and lower extremities are a function of the maximum and the minimum of 3D distance between the virtual and detected needles along the respiratory cycle can be displayed and the current 3D distance is displayed in real time in said gauge.

Another example of representation of the distance is a set D3 of concentric circles, the inner one representing the smaller distance and the outer one representing the larger distance along the respiratory cycle. The circle in dotted lines represents in real time the current distance of the detected needle tip with respect to the plane of the slice 10. Such a representation is a variant of the gauge D2.

Another example of representation of the distance is merely an indication of its numerical value D4.

Another example is a representation of the evolution of the distance with time. The curves D5 show on the one hand the evolution of the distance between the insertion point of the detected needle and the plane of the slice 10 with time, and on the other hand the evolution of the distance between the detected needle tip and the plane of the slice 10 with time, respectively.

Whatever the type of representation displayed, it evolves as the needle guide is moved by the user. The user can thus use the information displayed to check that the orientation and position of the needle guide may allow reaching the target.

With reference to FIG. 6, the representation of the distance can also be displayed in the 3D medical image.

For example, a circle D1 whose diameter depends on the distance between the detected needle tip and the virtual needle can be displayed on the tip of said detected needle, along with the value of said distance (here, 5 mm), whereas the value of the distance between the insertion point of the detected needle and the insertion point of the virtual needle (here, 10 mm) is displayed.

The representation of the relative position of the virtual needle with respect to the at least one detected needle can also be based on a set of transparency levels of the detected needle in 3D or of the projection of the detected needle in the plane containing the virtual needle (see FIG. 5). For example, the representation of the detected needle is all the more opaque that the needle is close to the virtual needle.

The representation of the relative position of the virtual needle with respect to the at least one detected needle can also be based on a set of thickness levels of the detected needle in 3D or of the projection of the detected needle in the plane containing the virtual needle (see FIG. 5). For example, the representation of the detected needle is all the more thick that the needle is close to the virtual needle. This explains the lozenge shape of the projection of the detected needle in FIG. 5.

Of course, two or more of these various representations can be combined and displayed together. In addition, the skilled person may select any other way of representing the distance without departing from the scope of the invention.

Advantageously, the respiration of the patient can be taken into account in order to determine an optimal instant for the user to further push the needle into the patient's body.

To that end, an instant of the respiratory cycle of the patient at which the virtual needle is closest to the detected needle is determined. The virtual position of the needle at said instant is then registered to the detected needle. Then, the representation of the virtual needle with respect to the detected needle is displayed again.

Besides, the determination of said instant of the respiratory cycle of the patient at which the virtual needle is closest to the detected needle can be used to provide an information to the user to push the needle into the patient's body at said instant, since this will give the best chance to reach the target. Indeed when both virtual and real needle coincide, it is considered that the patient breathing is at the same cycle position than it was when the 3D image was acquired. Therefore this method offers a virtual synchronization of time between the 3D image and the localization data.

According to a second embodiment illustrated in FIGS. 7-9, the 3D image contains the trace of at least one detected needle which is different from the needle that is introduced into the patient's body and which has already been inserted into the patient's body and has reached the target.

In the embodiments of FIGS. 7-9, three needles 2*a'*, 2*b'* and 2*c'* are detected in the 3D image 1 and have their tip in the target T. The needle to be additionally inserted in the target is coupled to a needle guide 3 which contains a tracker to be navigated with respect to the 3D image by the navigation system.

The reference 2*v* represents the virtual needle.

As shown in the right part of FIGS. 7 and 8, a slice 10 according to a plane containing the axis of the virtual needle is displayed with the trace of the detected needles 2*a'*, 2*b'*, 2*c'* projected in said plane and the target T.

The 2D or 3D distance between the virtual needle and each detected needle is calculated as explained above.

The indication of the distance between the virtual needle and each detected needle is represented in the similar way as already described with reference to FIGS. 5 and 6. These representations are thus not described again in detail.

For example, as shown in FIG. 7 (left), three gauges D2*a*, D2*b*, D2*c* are displayed.

Alternatively or in combination with the above representation, a circle D1*a*, D1*b*, D1*c* is centered on the projection of each respective detected needle, the radius of each circle depending on the distance between said detected needle and the virtual needle.

Alternatively or in combination with at least one of the above representations, the numerical value D4a, D4b, D4c of the distance between the virtual needle and each respective detected needle is displayed.

Alternatively or in combination with at least one of the above representations, curves D5 illustrated the evolution of the distance with time is displayed.

FIG. 8 illustrates an embodiment which is substantially similar to the one of FIG. 7, apart from the fact that the indication of the distance between the virtual needle and each detected needle is represented by a respective circle D1', D2', D3' whose radius depends on said distance.

As shown in FIG. 9, the representation of the distance can also be displayed in the 3D medical image 1. Numerical values of the distance between each detected needle and the virtual needle—and/or between two detected needles—can be displayed.

As already described above, a set of transparency levels and/or of thickness levels can also be applied to each detected needle.

As shown in FIGS. 5-9, it is also useful to display a 3D representation of the complete scene containing the previously detected needles as 3D line segments, as well as the navigated needle in real-time as another line segment, and also the target (e.g. tumor) as a surface, with indications of the relative 3D distances in addition.

With this displayed information, the user is capable of determining the position and orientation needed for the navigated needle in order to distribute the needles optimally over the target.

The invention claimed is:

1. A system for planning introduction of a needle in a patient's body, comprising:

a needle guide configured to be coupled to a needle;

a localization system configured for tracking the needle guide with respect to the patient's body, the localization system being coupled to (i) a needle tracker attached to the needle guide and (ii) a reference marker adapted to be attached to the patient's body to determine a spatial position and orientation of the needle guide relative to the reference marker;

a processor configured for receiving a 3D image, wherein the 3D image includes the reference marker and a part of the needle that has already been inserted into the patient's body, determining a virtual position and orientation of the needle with respect to the 3D image using localization data of the needle guide, thereby defining a virtual needle having said virtual position and orientation, detecting a part of the needle that has already been inserted into the patient's body as a trace in the 3D medical image, computing a distance between the virtual needle and the detected needle, and determining a representation of the computed distance;

a display coupled to the processor for displaying a representation of the virtual needle and the representation of the computed distance between the virtual needle and the detected part of the needle.

2. The system of claim 1, wherein the needle guide is selected from:

(i) a guide in which the needle is adapted to be slidingly arranged; and (ii) a guide configured to be rigidly attached to the needle.

3. The system of claim 1, wherein the processor is configured to implement an image processing algorithm to detect the at least one inserted needle in the 3D medical image.

4. The system of claim 1, wherein the processor is configured to detect the at least one inserted needle by using the position and orientation of the needle guide determined by the localization system to initialize an algorithm adapted to detect the inserted needle.

5. A non-transitory computer program product comprising computer-readable instructions which, when loaded and executed on the processor of a system according to claim 1, perform the steps of:

receiving a 3D image, wherein the 3D image includes the reference marker and a part of the needle that has already been inserted into the patient's body;

determining a virtual position and orientation of the needle with respect to the 3D image using localization data of the needle guide;

detecting at least one inserted needle as a trace in the 3D medical image;

computing a distance between the virtual needle and the detected needle;

determining a representation of the computed distance; and displaying a representation of the virtual needle and the representation of the computed distance between the virtual needle and the detected part of the needle.

6. A system for planning introduction of a needle in a patient's body, comprising:

a needle guide configured to be coupled to a needle;

a localization system configured for tracking the needle guide with respect to the patient's body, the localization system being coupled to (i) a needle tracker is-arranged inside the needle and (ii) a reference marker adapted to be attached to the patient's body to determine a spatial position and orientation of the needle guide relative to the reference marker;

a processor configured for receiving a 3D image, wherein the 3D image includes the reference marker and a part of the needle that has already been inserted into the patient's body, determining a virtual position and orientation of the needle with respect to the 3D image using localization data of the needle guide, thereby defining a virtual needle having said virtual position and orientation, detecting a part of the needle that has already been inserted into the patient's body as a trace in the 3D medical image, computing a distance between the virtual needle and the detected needle, and determining a representation of the computed distance;

a display coupled to the processor for displaying a representation of the virtual needle and the representation of the computed distance between the virtual needle and the detected part of the needle.

7. The system of claim 1, wherein the processor is configured for:

determining an instant of a respiratory cycle of the patient at which the virtual needle is closest to the detected needle; and registering the virtual position of the needle at said instant to the detected needle;

and wherein the display is configured for displaying again a representation of the distance between the virtual needle and the detected needle.

8. The system of claim 1, wherein the processor is configured for determining an instant of a respiratory cycle of the patient at which the virtual needle is closest to the detected needle and providing an information to a user to push the needle into the patient's body at said instant.

9. The system of claim 1, wherein the representation of the computed distance between the virtual needle and the detected needle comprises an indication of at least one 2D or 3D distance selected from:

(i) a 3D distance from a 3D point of the detected needle to a closest 3D point of the virtual needle, wherein the 3D point is a center of an active part of the needle;

(ii) a 3D distance between a line representing the detected needle to a line representing the virtual needle;

(iii) a 3D distance between either a 3D point of the detected needle and a line representing the virtual needle or a 3D point of the virtual needle and a line representing the detected needle, wherein the 3D point is a center of an active part of the needle;

(iv) 3D distances between either points of the detected needle and a plane containing the virtual needle or points of the virtual needle and a plane containing the detected needle;

(v) a 3D distance between either a line representing the detected needle and a plane containing the virtual needle or a line representing the virtual needle and a plane containing the detected needle; and (vi) a 2D distance between either the virtual needle tip and a closest point along a projection of the detected needle in a plane containing the virtual needle or the detected needle tip and a closest point along a projection of the virtual needle in a plane containing the detected needle.

10. The system of claim 9, wherein the display is configured for displaying said at least one 2D or 3D distance in at least one of the following formats:

a number corresponding to a numerical value of said distance;

a gauge with extremities corresponding to a function of a maximum and a minimum of these 3D distances along a respiratory cycle;

a curve showing an evolution of the distance with time;

a set of transparency levels of the detected needle in 3D or of a projection of the detected needle in a plane containing the virtual needle;

a set of thickness levels of the detected needle in 3D or of the projection of the detected needle in a plane containing the virtual needle; or a circle displayed on a plane containing the virtual needle, centered on a projection of a tip of the detected needles on the given plane and which radius is a function of said indicated 2D or 3D distance.

11. A system for planning introduction of a needle in a patient's body, comprising:

a needle guide configured to be coupled to a needle;

a localization system configured for tracking the needle guide with respect to the patient's body, the localization system being coupled to (i) a tracker attached to the needle guide and (ii) a reference marker adapted attached to the patient's body to determine a spatial position and orientation of the needle guide relative to the reference marker;

a processor configured for receiving a 3D image, wherein the 3D image includes the reference marker and a part of a needle that has already been inserted into the patient's body;

determining a virtual position and orientation of the needle with respect to the 3D image using localization data of the needle guide, thereby defining a virtual needle having said virtual position and orientation, detecting at least one inserted needle as a trace in the 3D medical image, and computing a distance between the virtual needle and the detected needle, wherein the trace detected in the 3D medical image is a trace of an additional needle distinct from the virtual needle and that has already been inserted into the patient's body; and a display coupled to the processor for displaying a representation of the virtual needle and a representation of the computed distance between the virtual needle and the at least one detected additional needle.

12. The system of claim 11, wherein the representation of the computed distance between the virtual needle and the at least one detected additional needle comprises an indication of at least a 2D or 3D distance selected from:

(i) a 3D distance from a 3D point of the detected additional needle to a respective 3D point of the virtual needle, wherein the 3D point is a center of an active part of the needle;

(ii) a 3D distance between a line corresponding to the detected additional needle to a line representing the virtual needle;

(iii) a 3D distance between either a 3D point of the detected additional needle and a line representing the virtual needle or a 3D point of the virtual needle and a line representing the detected additional needle, wherein the 3D point is a center of an active part of the needle;

(iv) 3D distances between either points of a detected additional needle and a plane containing the virtual needle or points of a virtual needle and a plane containing the detected additional needle;

(v) a 3D distance between either a line representing a detected additional needle and a plane containing the virtual needle or a line representing the virtual needle and a plane containing the detected additional needle;

(vi) a 2D distance between either the virtual needle tip and a projection of the detected additional needle in a plane containing the virtual needle or the detected additional needle and a projection of the virtual needle in a plane containing said detected additional needle; and (vii) a 3D distance between tips of the detected additional needles.

13. The system of claim 12, wherein the display is configured to display said at least one 2D or 3D distance in at least one of the following formats:

a number corresponding to the numerical value of said distance;

a curve showing the evolution of the distance with time;

a set of transparency levels of the detected additional needles in 3D or of a projection of the detected additional needles in a plane containing the virtual needle;

a set of thickness levels of the detected additional needles in 3D or of the projection of the detected additional needles in a plane containing the virtual needle;

a sphere centered on a tip of the detected additional needles and whose radius is a function of said distance; or a circle displayed on a plane containing the virtual needle, centered on a projection of a tip of the detected additional needles on the given plane and which radius is a function of said distance.

14. The system of claim 11, wherein the processor is configured for determining an instant of a respiratory cycle of the patient where the virtual needle is at an optimal position relative to each detected additional needle and providing an information to a user to push the needle into the patient's body at said instant.

15. A non-transitory computer program product comprising computer-readable instructions which, when loaded and executed on the processor of a system according to claim 11, perform the steps of:

receiving a 3D image, wherein the 3D image includes the reference marker and a part of a needle that has already been inserted into the patient's body;

determining a virtual position and orientation of a needle coupled to a needle guide with respect to a 3D medical image using localization data of the needle guide;

detecting at least one inserted additional needle as a trace in the 3D medical image;

computing a distance between the virtual needle and the at least one detected additional needle, wherein the trace detected in the 3D medical image is a trace of an additional needle distinct from the virtual needle and that has already been inserted into the patient's body; and determining a representation of the computed distance; and displaying a representation of the virtual needle and a representation of the computed distance between the virtual needle and the at least one detected additional needle.

* * * * *